United States Patent [19]

Wislocki

[11] 3,998,090
[45] Dec. 21, 1976

[54] SOIL COMPACTOR
[75] Inventor: Joseph P. Wislocki, Vicksburg, Miss.
[73] Assignee: The United States of America as represented by the Secretary of the Army, Washington, D.C.
[22] Filed: Nov. 7, 1975
[21] Appl. No.: 629,812
[52] U.S. Cl. .................. 73/12; 73/88 E; 73/432 R
[51] Int. Cl.² ............... G01N 1/28; G01N 33/24
[58] Field of Search ............ 73/12, 88 E, 432 R; 425/428

[56] References Cited
UNITED STATES PATENTS

| | | | |
|---|---|---|---|
| 921,287 | 5/1909 | Schmidt | 425/428 |
| 2,482,949 | 9/1949 | Jankovich | 425/428 X |
| 2,531,388 | 11/1950 | Black | 73/12 |
| 3,001,393 | 9/1961 | Greayer | 73/12 |
| 3,566,668 | 3/1971 | Browning et al. | 73/12 |

Primary Examiner—James J. Gill
Attorney, Agent, or Firm—John G. Mannix

[57] ABSTRACT

A soil compactor for laboratory use to systematically and controllably compact specimens of soil and earth-rock mixture materials. The raising of a drop hammer after each strike to a pre-selected height is accomplished automatically by the use of a pneumatic cylinder in conjunction with sensing valves. A counter and deactivation valve are also provided so that the system will automatically shut off after the hammer drops a pre-determined number of times. Uniform compaction of each specimen is ensured by automatically rotating the specimen a pre-selected number of degrees after each strike by the hammer. The compactor is also vertically and horizontally adjustable so that specimens of various heights and widths can be accommodated.

4 Claims, 19 Drawing Figures

SOIL COMPACTOR

BACKGROUND OF THE INVENTION

This invention relates to soil compactors for use in laboratories to compact specimens of soil and earth-rock material, and more particularly to an apparatus for automatically controlling certain movements of the compaction hammer, which have heretofore required taxing manual control on the part of laboratory technicians.

In the field of laboratory equipment, the main concern is with accuracy and consistency. The prior art heretofore has depended on the ability of the operating technician to manually control the accuracy and consistency of the equipment. U.S. Pat. No. 2,531,388, issued to John W. Black, is an example of the soil compacting equipment in operation today. This equipment requires constant attention by the operator both in manually raising and dropping the hammer and in continually rotating the specimen in exact increments to achieve uniform compaction.

SUMMARY OF THE INVENTION

The present invention relieves the problems discussed above by providing for automatic control of the hammer movements and specimen rotation. A control system is provided wherein the length of the hammer drop and number of strikes can be set and the machine then left completely unattended to perform the required operation. Further control is employed to ensure proper compaction by providing uniform rotation of the specimen turntable after each drop of the hammer.

DESCRIPTION OF THE PREFERRED EMBODIMENT

Referring more particularly to the drawings, the improved apparatus of the present invention comprises a U-shaped base 1, a pair of screw threads 2, mounted into the base 1, and a superstructure 3 attached to the screw threads for vertical movement, with respect to the screw threads, as they are rotated. As shown in FIGS. 1, 2, 7 and 8, rotation of the screw threads is accomplished by the use of an electric motor 4 which, through shaft 4a, rotates a worm 4b and a worm wheel 4c. Screw threads 2 are fixedly mounted to the worm wheel 4c and therefore rotate with it. Note that the worm gear does not impart vertical movement to the screw threads (see FIGS. 7 and 8) but merely rotates them in a clockwise or counterclockwise direction. Since there are two screws threads (see FIG. 1), the superstructure is impeded from rotating with the screw threads and it is forced up or down, depending on the direction of screw rotation, as the threads rotate within the base.

Figure 17:
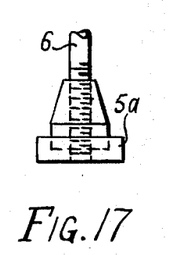
FIGS. 17 thru 19 illustrate various size hammer heads which can be attached to the hammer rod.
Figure 18:
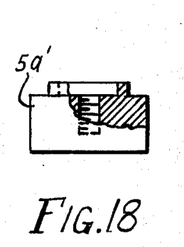
Figure 19:
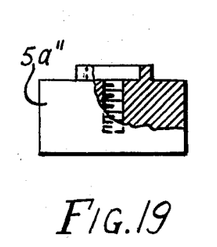

The superstructure carries a drop hammer means 5, comprising a hammer head 5a and a hammer rod 6. Note that FIGS. 17–19 show various sizes of hammer heads which can be attached to rod 6. Guide means 48 and gripping means 7 are provided for holding the hammer means at any particular height above a specimen 8 which is to be compacted within a mold 9. Looking at FIGS. 1 and 4, the gripping means 7 comprises two identical grippers 10 mounted on a right angle shaped platform 11. Each gripper comprises a semi-circular engagement member 12 mounted on an L-shaped member 13, which is pivoted at a lowermost point to the platform 11 by a hinge 13 and hinge pin 14', or other suitable pivot means.

Figure 4:
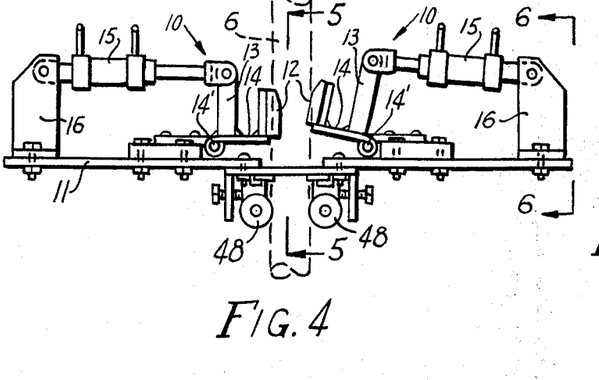
FIG. 4 is a partial sectional view taken along the line 4—4 of FIG. 2 and shows the gripping means.
Figure 5:
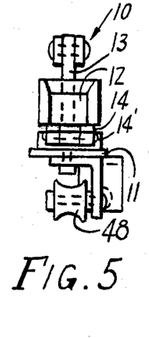
FIG. 5 is a partial sectional view taken along the line 5—5 of FIG. 4.
Figure 6:
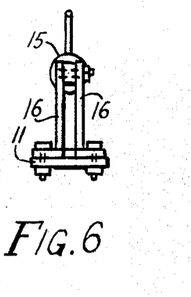
FIG. 6 is a partial sectional view taken along the line 6—6 of FIG. 4.
Figure 7:
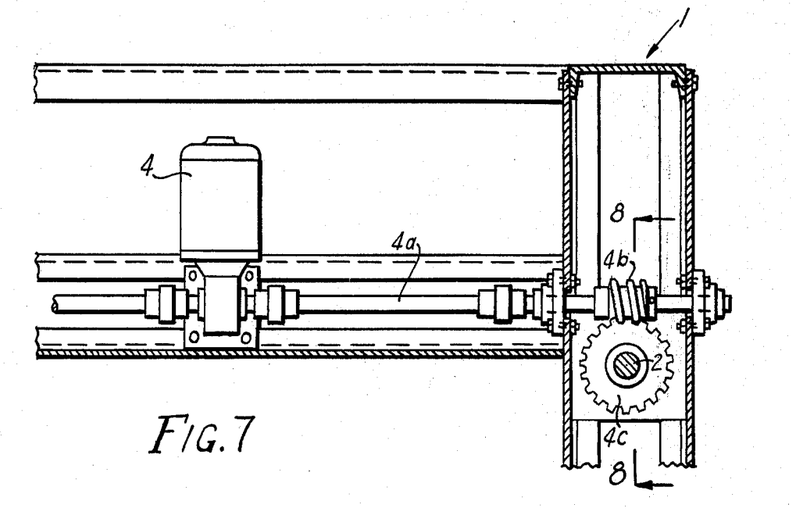
FIG. 7 is a partial sectional view taken along the line 7—7 of FIG. 1 and shows a worm gear and electric motor by which the superstructure is raised and lowered.
Figure 8:
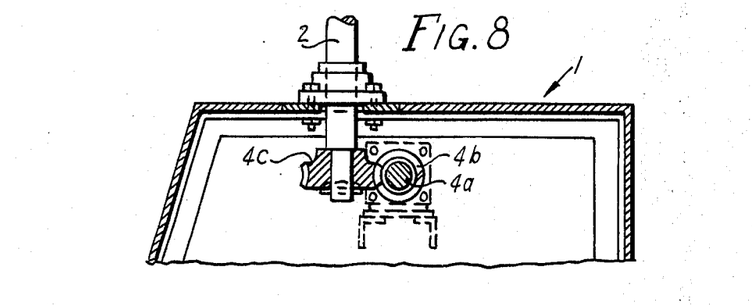
FIG. 8 is a partial sectional view taken along the line 8—8 of FIG. 7 and shows an enlarged sectional view of the worm gear.

Each gripper 10 is moved between the hold and and release positions by an air cylinder 15, which is pivoted at one end to an uppermost point of L-shaped member 13, and pivoted at its other end to a mounting bracket 16, which in turn is attached to the horizontal portion of the platform 11.

Figure 13:
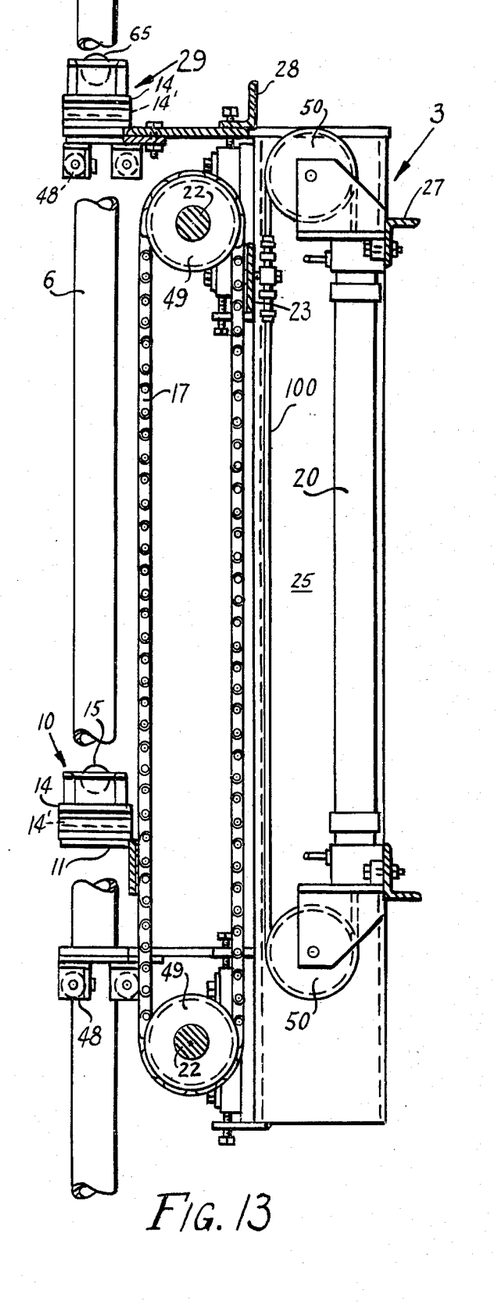
FIG. 13 is a side elevational view taken along the line 13—13 of FIG. 3 and shows the mechanism used to raise and lower the drop hammer.

The platform 11, holding the gripping means 7, can be raised or lowered with respect to the superstructure 3 by activation of a cable air cylinder 20 (FIG. 13). Looking at FIGS. 1 & 13, the vertical flange portion of platform 11 is fixedly attached by bolts 21 to the front face of continuous chains 17, which chains are mounted on sprockets 49, fixed on cylindrical cross bars 22 which are journaled for rotation into the superstructure 3. The rear faces of chains 17 are connected by cable tie bar 23 to a continous cable 100, which is mounted around pulleys 50 and forms part of cable air cylinder 20. Therefore, as the cable cylinder is activated the rear face of the continuous chain 17 moves up or down thus causing the platform 11 and gripping means 7 to move in the opposite direction.

The superstructures 3 comprises two vertical beam members 25 which are attached to screw threads 2 by wing members 26. Cross supports 27 are added for strength. An angle member 28 is fixedly mounted between the top ends of the vertical beams 25. A pair of auxiliary grippers 29, normally biased in the open position, are mounted on the horizontal flange of the angle member 28 to serve a twofold purpose. First, as a safety feature they hold the hammer means while adjustment or repair work is being done to the main gripping means. Second, they assist in jogging the hammer up or down with respect to the main grippers. By way of example, in order to grip the hammer rod at a point below the gripping point shown in FIG. 1, the platform 11 is first raised as high as it will go, then the normally open auxiliary grippers 29 are applied while releasing the main grippers 10, after which the platform 11 is lowered to the desired point on the hammer rod. If the desired point is still below the lowermost reach capability of the platform, the main grippers will be applied at the lowermost point possible on the rod, the auxiliary grippers released, and the above procedure repeated until the desired point on the hammer rod is within the range of the main grippers.

Figure 9:
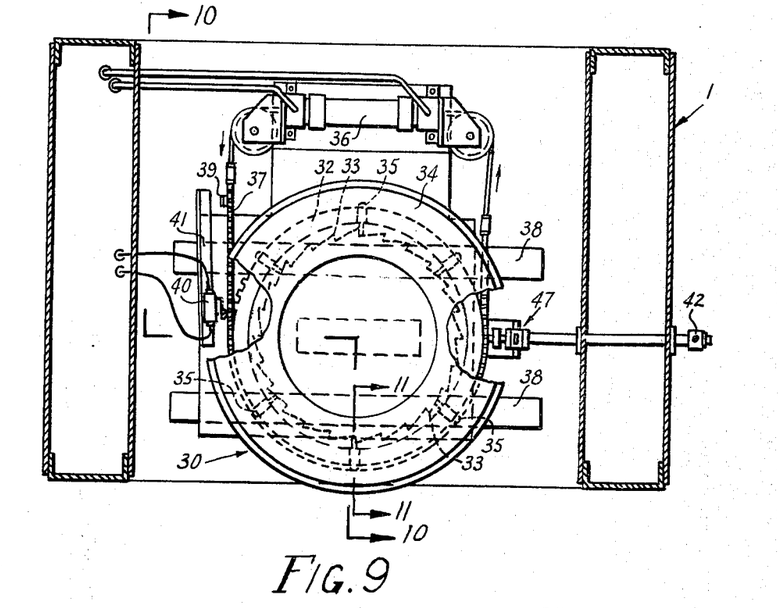
FIG. 9 is a top view of the turntable assembly taken along the line 9—9 of FIG. 1.
Figure 10:
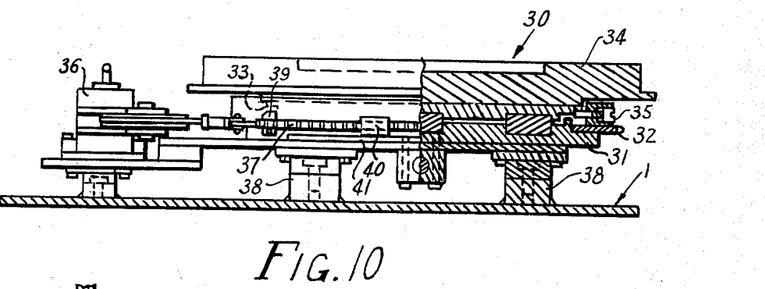
FIG. 10 is a side elevational view of the turntable assembly taken along the line 10—10 of FIG. 9.
Figure 11:
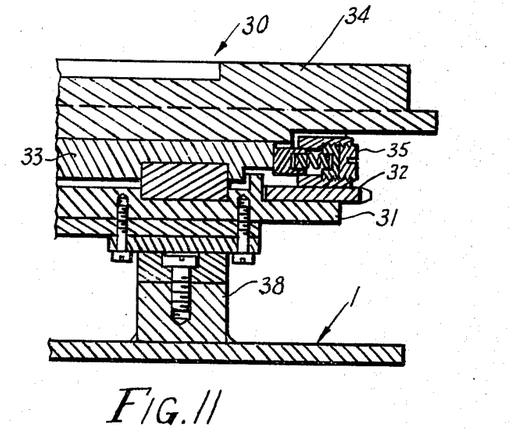
FIG. 11 is an enlarged side elevational view taken along the line 11—11 of FIG. 9.
Figure 12:
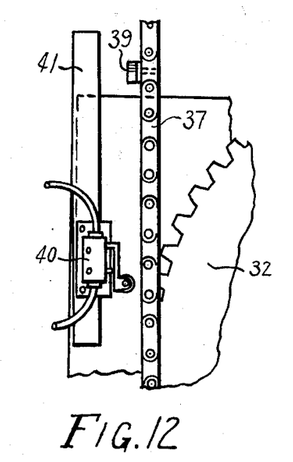
FIG. 12 is an enlarged top view of the pawl plate, limit valve and limit trip mechanism.

Positioned on the horizontal portion of the frame base plate 1 is a turntable assembly 30 (see FIG. 9–12), comprising a turntable base plate 31, a standard sprocket toothed pawl plate 32, a ratchet plate 33, a mold base platen 34 and numerous spring loaded retractable pawls 35, contained within the pawl plate. The turntable assembly is mounted on guide rails 38 that are fixed to the frame base plate 1. By means of a screw and nut assembly 47 mounted between the rails, the turntable can be positioned horizontally in one plane to accommodate various size molds. Positioning is accomplished by actuating the ratchet handle 42 (in FIG. 1 & 2). The mold base platen 34 is fixedly connected to the ratchet plate 33, while the pawl plate 32 is free floating between the mold base platen 34 and base plate 31. As shown in FIG. 9, the pawl plate rotates freely with respect to the ratchet plate in the clockwise direction, but is impeded from free rotation in the counterclockwise direction by the action of pawls 35 as they mesh with the ratchet teeth of ratchet plate 33. Rotation of the turntable assembly 30 is accomplished by actuation of a second cable air cylinder 36, mounted on base 1, just to the rear of the turntable assembly. A chain 37 is connected to both cable ends of the cable cylinder 36 and meshes with the teeth of pawl plate 32. Fastened to chain 37 is a trip 39 which engages a limit valve 40 connected for longitudinal movement on a track 41 which is mounted on base 1. Looking at FIGS. 9 and 12, as the cable of the cable cylinder 36 moves in the direction of the arrow, the chain 37 and pawl plate 32 move in the counterclockwise direction, until the trip 39 on the chain activates the limit valve 40 causing the cable cylinder to stop and reverse direction. While the pawl plate 32 was moving in the counterclockwise direction the ratchet plate 33 and main platen 34 rotated with it, since at least one of the pawls 35 was in engagement between the pawl plate and ratchet plate. But, since the pawl plate is free to rotate with respect to the ratchet plate in the clockwise direction, when the cable cylinder 36 is reversed by the limit valve, only the pawl plate moves back to begin a new cycle. Note that the amount of rotation of the turntable assembly can be controlled by adjusting the position of the limit valve 40. Also note that due to the large number of pawls incrementially spaced, there is always a pawl in position to instantly start rotation of the ratchet plate in the counterclockwise direction. As mentioned previously, the limit valve 40 is mounted on track 41 for movement back and forth. This track can be incrementially marked in degrees of turntable rotation so that accurate uniform compactions of different soil specimens can be made.

OPERATION

Figure 16:
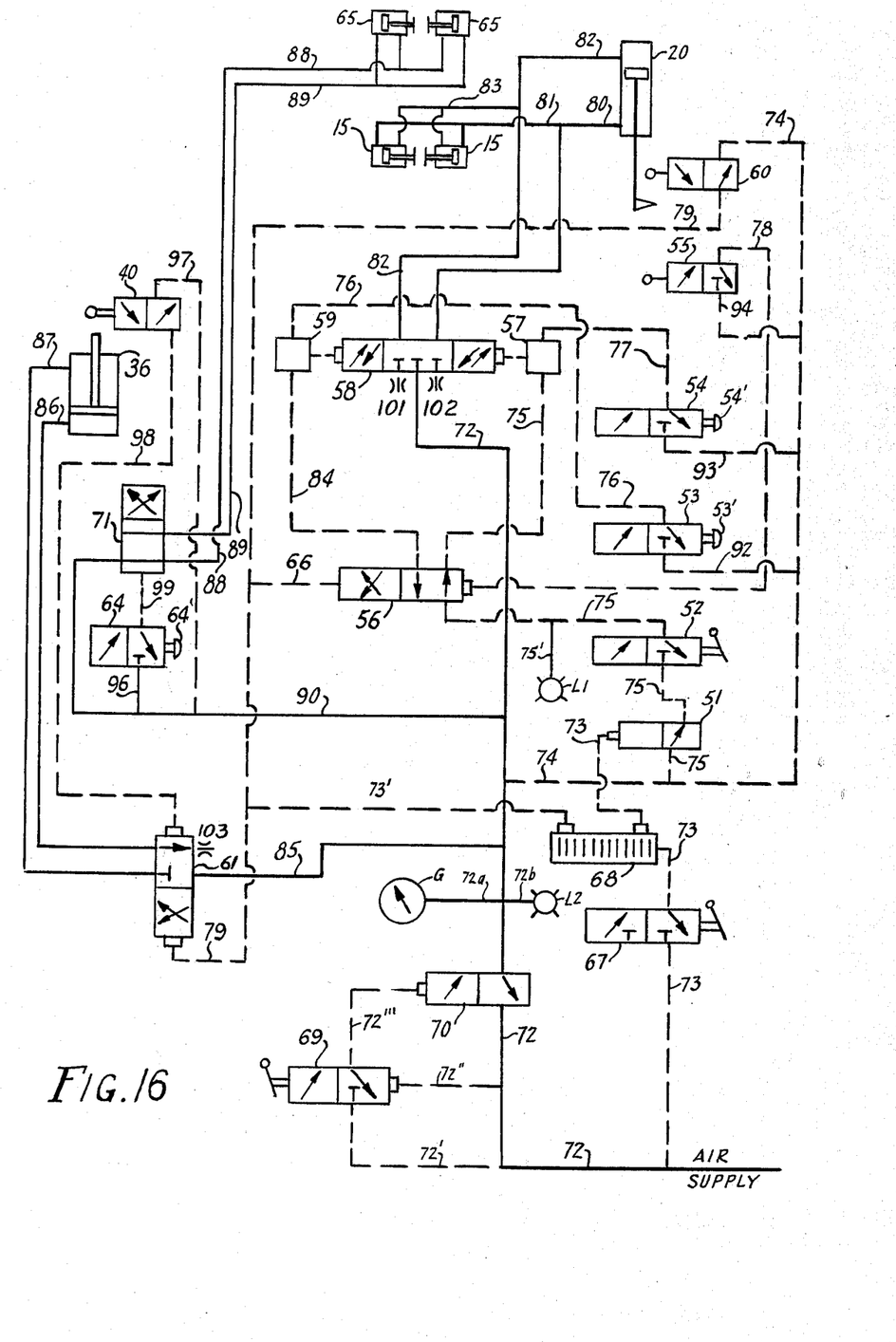
FIG. 16 is a schematic diagram of the fluid system used to control the automatic operation of the present invention.

Operation of the automatic compacting system will now be described. FIG. 16 of the drawings shows the system in its closed down or nonoperative state. The solid lines designate the main operating fluid flow lines. The dotted lines designate the secondary fluid flow lines. The only function of the lines and valves in secondary fluid circuit is to control the opening and closing of valves in the main circuit. The actual work is performed by the fluid in the main solid line circuit. The fluid system is initially activated by manually switching three-way toggle valve 69 to the open position, which in turn forces open 3 way valve 70, thus unblocking main fluid flow line 72. Three-way toggle valves 52 and 67 should also be manually moved to the open position at this point in the operation. Valve 52 controls the continuous operation of the compaction process, since it signals the main four-way valve 58 when to start and stop the continuous tamping by the hammer means 5. Valve 67 simply activates a counter 68. The counter can be set for any number of compaction strikes desired and when this predetermined number is reached valve 52, through valve 51, will be forced to the closed position and the continuous compaction operation will be stopped.

Figure 3:
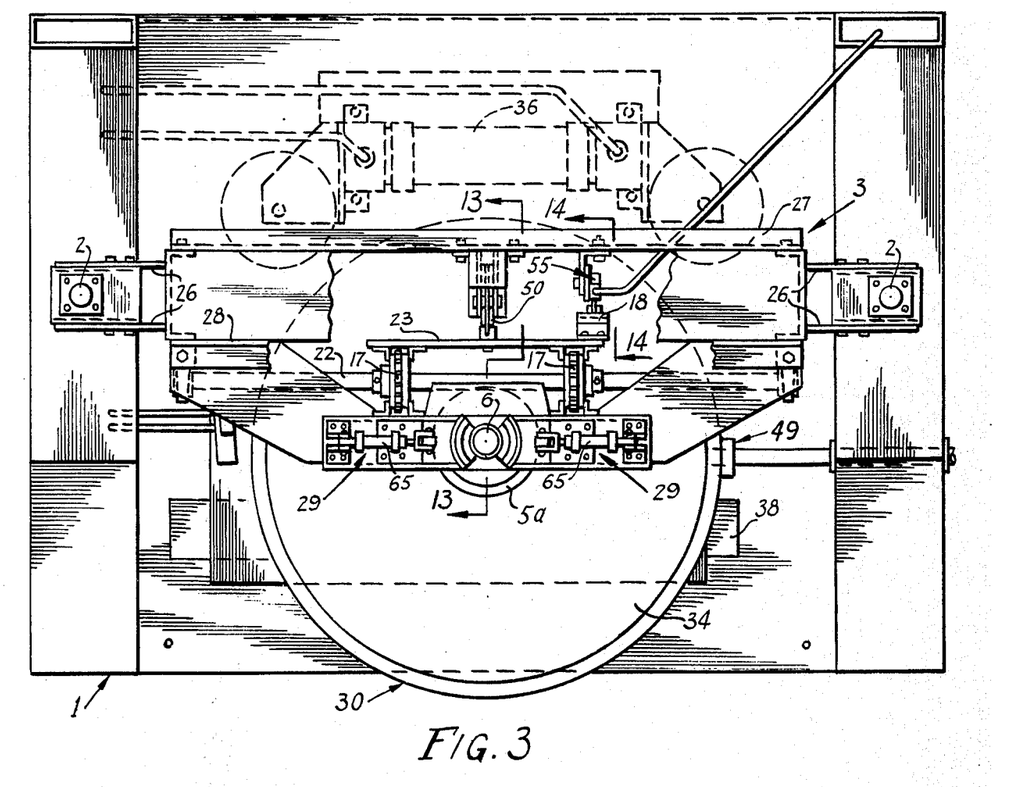
FIG. 3 is a top view showing the physical relationship among the turntable, the grippers, the cable air cylinder which raises and lowers the grippers, and the limit means which controls the automatic raising and lowering of the grippers.
Figure 14:
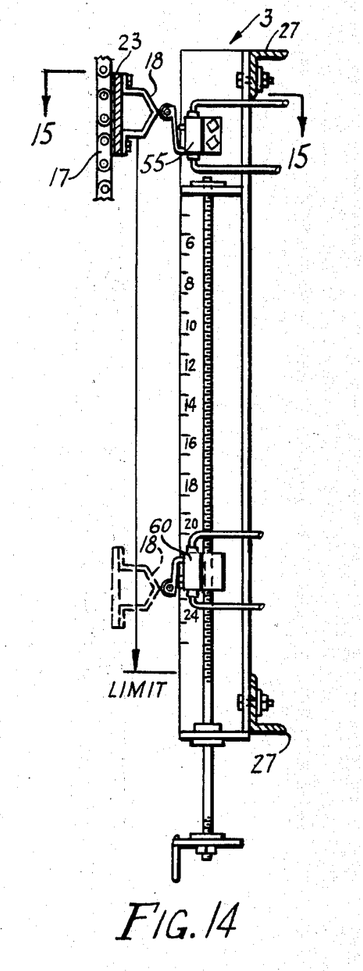
FIG. 14 is a side elevational view taken along the line 14—14 of FIG. 3 and shows the limit mechanism used to control the distance of the hammer drop.
Figure 15:
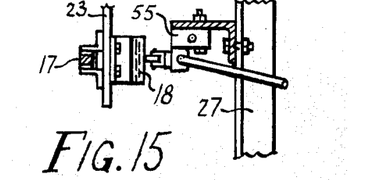
FIG. 15 is a top view taken along the line 15—15 of FIG. 14.

To further explain the pneumatic circuit one complete cycle of the compaction process will now be followed through the circuit. With valves 69, 52, and 67 in the open position, the operation can begin. Fluid flows from the main supply into lines 72, 85, 90 and 74. Some fluid in line 74 is diverted into line 75 and through valves 51, 52 and 56 to an alternating or shuttle valve 57, which actuates the main four way valve 58 to communicate the main fluid flow line 72 with line 80. This causes the piston in cable cylinder 20 to move upward until a three-way limit valve 60 is actuated by a grip mechanism 18 on chain 17 (FIG. 14 shows actual linkage while FIG. 16 showing is symbolic). Simultaneously, fluid is also directed from line 80 to line 81 to actuate cylinders 15, thus forcing the grippers 10 into engagement with the hammer rod 6. Looking at FIG. 13, it should be noted that as the piston is cable cylinder 20 moves up the cable actuates the chain 17 in the clockwise direction, raising the platform 11 which holds the two grippers 10 now engaging the hammer rod 6. So, as the piston of cylinder 20 is moved upward the hammer is also being raised. As stated previously this raising continues until the trip mechanism 18, mounted on the chain 17, activates valve 60 (see FIGS. 3, 13 and 14). This activation causes fluid to flow through valve 60 into line 79, which causes a four-way valve 56 through line 66, and another four-way valve 61 to reverse connections. With respect to valve 61, this opens valve 61 to the main supply flow so that fluid passes from line 85 to line 86, thus moving the piston in cylinder 36. Looking at FIGS. 9 and 12, this rotates the turntable assembly 30 in a counterclockwise direction until trip mechanism 39 mounted on chain 37, actuates a three-way limit valve 40, which in turn stops rotation of the turntable. As valve 40 is actuated, it opens line 98 to fluid flow from lines 90 and 97, which reverse valve 61, changing the flow through main line 85 from line 86 to line 87 and causing the piston of cylinder 36 to move down as shown in FIG. 16, bringing back with it chain 37, trip mechanism 39 and the pawl plate 32. The ratchet plate 33 will not rotate back with the pawl plate as the pawl plate is returned by chain 37, since, as explained earlier, there is free rotation of the pawl plate with respect to the ratchet plate in the clockwise direction. With respect to valve 56, which was moved simultaneously with valve 61 by the fluid flow in line 79 and 66, this movement of valve 56 opens line 84 allowing fluid to reach a second alternating or shuttle valve 59. This activates the main four-way valve 58 to communicate the main fluid flow line 72 with line 82. In turn, this causes fluid to flow into line 83 to the pistons 15 to release the grippers 10, thus allowing the hammer to fall on the specimen 8. Simultaneously, fluid from line 82 forces the piston of cylinder 20 down, until the trip mechanism of a three-way limit valve 55 (see also FIG. 14) is actuated. When the piston of cylinder 20 goes down, platform 11, which is raised and lowered by cylinder 20, will also descend, due to the counterclockwise rotation of chain 17, until the trip mechanism of limit valve 55 is actuated. When this occurs flow from line 94 is allowed to pass through valve 55 into line 78. This flow reverses the line connections in valve 56 again so that fluid flows into line 75, actuating the shuttle valve 57 which opens four-way valve 58. This communicates the main flow line 72 with line 80 thus causing the grippers 10 to engage the hammer rod 6 again and cylinder 20 to begin raising the platform 11 again. This complete cycle will continue until the predetermined number set on the counter 68 is reached. When valve 51 will cause the run valve 52 to close thus stopping the entire cycle.

The height of the hammer drop can be varied in the following manner. As shown in FIG. 14, limit valve 55 is fixed, but limit valve 60 is vertically adjustable. Since limit valve 60 determines the uppermost movement of platform 11, which is also the point at which the grippers 10 release the hammer means 5, the lower the limit valve 60 is set, the higher the hammer head 5a will be when the limit valve 60 is actuated and the longer distance the hammer will drop before hitting the specimen 8.

To assist in the jogging operation referred to earlier, there are two manually operable three-way button valves 53 and 54 shown in FIG. 16. Each has an activation button 53' and 54' which holds the respective valves open as long as they are pushed into the valve. These valves, when open, activate either the shuttle valve 57, or the shuttle valve 59, thus lowering or raising the platform 11 and gripping means 7. Therefore, the platform can easily be raised or lowered by simply holding in the appropriate activation button 53' or 54', until the desired point is reached and then releasing the button, thus stopping movement.

The auxiliary grippers 29 (see FIGS. 1 and 3), also referred to earlier, are identical in design to the main grippers 10. Each gripper is activated by a cylinder 65, which is controlled by fluid through another three-way button valve 64. Valve 64 has a valve button 64' similar to valve buttons 54' and 53'. When button 64' is in its normal out position, fluid from main line 72 flows through line 90 and valve 71 into line 88 where it forces the pistons of cylinders 65 toward the outward direction and thus holds the grippers 29 in the disengaged position. When button valve 64 is activated by pushing in button 64', valve 71 will reverse connections so that fluid from line 90 will now flow into line 89 and the fluid in line 88 will be vented to the atmosphere through valve 71 thus forcing the pistons of cylinders 65 toward each other and thereby forcing the grippers 29 into the engaged position. Upon release of the button 64' valve 71 will return to its normal position and the auxiliary grippers will be disengaged.

Figure 1:
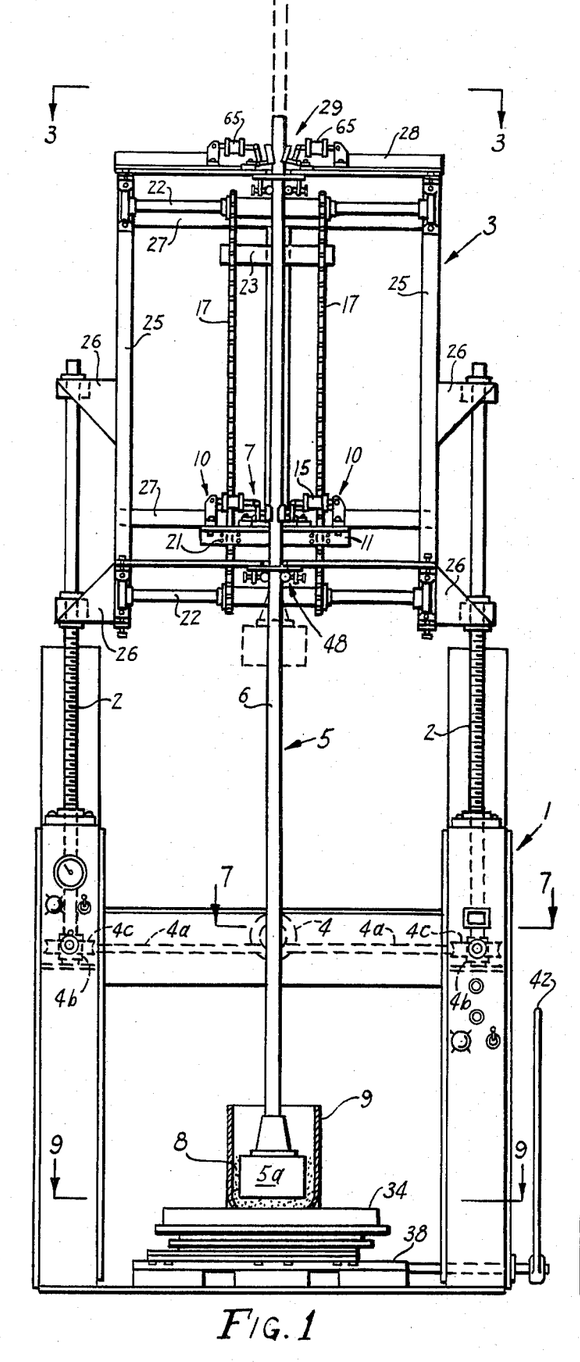
FIG. 1 is a front elevational view of a soil compactor embodying the invention.
Figure 2:
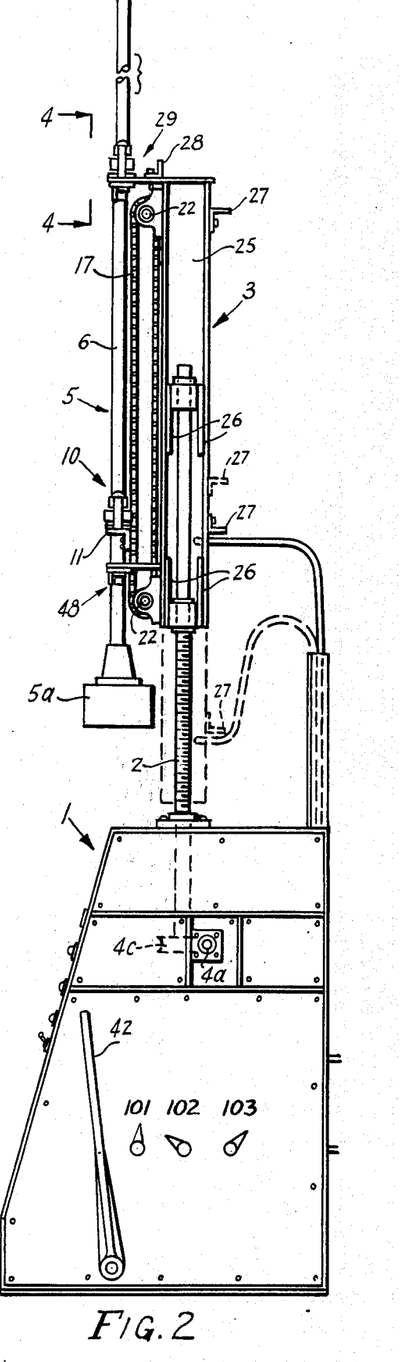
FIG. 2 is a side elevational view of a soil compactor embodying the invention.

To control or to vary the speed of the drop hammer 5, in either direction, pneumatic adjustable flow control valves 101 and 102 are installed in the lines out of the exhaust ports of valve 58 as shown in FIG. 16. To control or vary the speed of the turntable base plate 31 in the counterclockwise direction, a pneumatic adjustable flow control valve 103 is installed in the line out of the exhaust port of valve 61. The flow control valves 101, 102 and 103 are located on the outside of the machine as shown in FIG. 2.

Note that even though the automatic system has been shown to be totally pneumatic, it could also be a combination pneumatic and electrical by substituting electric solenoids for the presently shown pneumatic actuating valves to control the pneumatic system.

While the preferred embodiment has been illustrated and described, it will be understood that changes in the construction may be made within the scope of the appended claims without departing from the spirit of the invention.

I claim:
1. Apparatus for compacting specimens of soil and earth rock materials comprising, in combination:
   a. a base;
   b. a superstructure, mounted above said base;
   c. a hammer means;
   d. gripping means mounted on said superstructure for holding and releasing said hammer means;
   e. means for raising and lowering said gripping means with respect to said superstructure comprising a cable cylinder fixedly mounted on said superstructure, a continuous chain mounted on said superstructure, means for connecting the cable of said cable cylinder to said continuous chain, a platform for mounting said gripping means thereupon and means for connecting said platform to said continuous chain;
   f. a rotatable platen mounted directly below said hammer means to hold a specimen to be compacted;
   g. means to rotate said platen in response to the completion of each stroke of said hammer means.
2. Apparatus for compacting specimens of soil and earth rock materials comprising, in combination:
   a. a base;
   b. a superstructure, mounted above said base;
   c. a hammer means;
   d. gripping means mounted on said superstructure for holding and releasing said hammer means;
   e. means for raising and lowering said gripping means with respect to said superstructure;
   f. a rotatable platen mounted directly below said hammer means to hold a specimen to be compacted;
   g. means to rotate said platen, in response to the completion of each compaction stroke of said ham- mer means, comprising a cable cylinder, a chain having one end connected to one end of said cable cylinder and the other end connected to the other end of said cable cylinder, a pawl plate having teeth in mesh with said chain, a ratchet plate concentrically fixed below said platen and mounted concentrically above said pawl plate, means to impede rotation of the ratchet plate with respect to the pawl plate in one direction while allowing free rotation in the opposite direction, whereby as rotation in one direction is imparted to the pawl plate by said cable cylinder, the ratchet plate and affixed platen will follow said pawl plate, but when the direction of rotation is reversed the ratchet plate and affixed platen will not follow said pawl plate.

3. Apparatus for compacting specimens of soil and earth rock materials comprising, in combination:
 a. a base;
 b. a superstructure, mounted above said base;
 c. a hammer means;
 d. two identical grippers mounted on a platform member on the superstructure for holding and releasing said hammer means, wherein each gripper comprises a pivot means, an L-shaped member mounted for pivotal movement on said pivot means, a semi-circular engagement member mounted on one arm of said L-shaped member and a cylinder connected between the other arm of said L-shaped member and said platform, whereby movement of said cylinder causes said L-shaped member to pivot about said pivot member thus retracting and extending said semi-circular engagement member;
 e. means for raising and lowering said gripping means with respect to said superstructure;
 f. a rotatable platen mounted directly below said hammer means to hold a specimen to be compacted;
 g. means to rotate said platen in response to the completion of each compaction stroke of said hammer means.

4. Apparatus for compacting specimens of soil and earth rock materials comprising, in combination:
 a. a U-shaped base member;
 b. a superstructure, mounted above said base and movable vertically with respect to said base;
 c. a hammer;
 d. gripping means mounted on said superstructure for holding releasing said hammer;
 e. means for raising and lowering said gripping means with respect to said superstructure;
 f. a rotatable platen mounted directly below said hammer to hold a specimen to be compacted;
 g. means to rotate said platen in response to the completion of each compaction stroke of said hammer;
 h. means to count the number of compaction strokes imparted to a given specimen;
 i. means to stop compaction in response to said counting means reaching a certain preselected number;
 j. trip means to limit the upper and lowermost travel of said gripping means;
 k. means for causing said gripping means to disengage said hammer in response to said gripping means reaching said upper travel limit, thus allowing said hammer to drop upon a specimen to be compacted;
 l. means for causing said gripping means to engage said hammer in response to said gripping means reaching said lowermost travel limit;
 m. auxiliary grippers fixedly mounted to said superstructure and concentric with said gripping means.

* * * * *